(12) United States Patent
Xu et al.

(10) Patent No.: US 12,004,928 B2
(45) Date of Patent: Jun. 11, 2024

(54) FOLDING DEVICE FOR DISPOSABLE HYGIENE ARTICLE

(71) Applicants: ZUIKO (SHANGHAI) CORPORATION, Shanghai (CN); ZUIKO CORPORATION, Osaka (JP)

(72) Inventors: Yi Xu, Shanghai (CN); Yasunori Shiraishi, Settsu (JP); Hideki Fujita, Settsu (JP)

(73) Assignees: ZUIKO (SHANGHAI) CORPORATION, Shanghai (CN); ZUIKO CORPORATION, Settsu (JP)

( * ) Notice: Subject to any disclaimer, the term of this patent is extended or adjusted under 35 U.S.C. 154(b) by 375 days.

(21) Appl. No.: 17/603,030

(22) PCT Filed: Apr. 10, 2020

(86) PCT No.: PCT/CN2020/084157
§ 371 (c)(1),
(2) Date: Oct. 12, 2021

(87) PCT Pub. No.: WO2020/207461
PCT Pub. Date: Oct. 15, 2020

(65) Prior Publication Data
US 2022/0192892 A1 Jun. 23, 2022

(30) Foreign Application Priority Data

Apr. 12, 2019 (CN) .......................... 201910292032.6
Apr. 12, 2019 (CN) .......................... 201920491298.9

(51) Int. Cl.
*A61F 13/00* (2024.01)
*A61F 13/15* (2006.01)

(52) U.S. Cl.
CPC .. *A61F 13/15747* (2013.01); *A61F 13/15764* (2013.01)

(58) Field of Classification Search
CPC ......... A61F 13/15747; A61F 13/15764; B65B 63/04
See application file for complete search history.

(56) References Cited

U.S. PATENT DOCUMENTS

| | | | | |
|---|---|---|---|---|
| 1,484,507 A | * | 2/1924 | Kohn | ...................... D06F 89/00 493/444 |
| 2,308,155 A | * | 1/1943 | Clegg | ..................... D06F 89/00 493/441 |

(Continued)

FOREIGN PATENT DOCUMENTS

| | | |
|---|---|---|
| CN | 102050356 A | 5/2011 |
| CN | 102050357 A | 5/2011 |

(Continued)

OTHER PUBLICATIONS

Sep. 27, 2022 Office Action issued in Japanese Patent Application No. 2021-560731.

(Continued)

*Primary Examiner* — Steven O Douglas
(74) *Attorney, Agent, or Firm* — Oliff PLC (57) ABSTRACT

A folding device for a disposable hygiene article includes: a first conveying portion along a first path; a second conveying portion along a second path extending in a direction intersecting with the first path; a folding mechanism to fold the disposable hygiene article between the first and second conveying portions; a driving mechanism connected to the folding component, to drive the folding component by performing reciprocating linear motion along the direction of the second path between a folding and retracted positions; and a guiding mechanism in an extension direction of the first path or by using the first path as a reference, a front end portion of the article to an opposite side of the second conveying portion. The driving mechanism includes at least one pulley directly connected to a servo motor and a (Continued)

synchronous belt wrapped around the outer circumference of the pulleys in a looping path.

10 Claims, 7 Drawing Sheets

(56) References Cited

U.S. PATENT DOCUMENTS

| | | | | |
|---|---|---|---|---|
| 3,339,914 | A | * | 9/1967 | Grantham .............. D06F 89/00 271/70 |
| 3,749,394 | A | * | 7/1973 | McCain ................ B42B 4/00 493/406 |
| 3,901,501 | A | * | 8/1975 | Kistner ................ B65H 45/18 493/450 |
| 4,109,902 | A | * | 8/1978 | Barrer ................. B65H 45/12 493/444 |
| 4,508,528 | A | * | 4/1985 | Hirsch ................. B65H 45/18 270/45 |
| 4,650,173 | A | | 3/1987 | Johnson et al. |
| 5,176,615 | A | * | 1/1993 | Munsch ............... B65H 45/161 493/427 |
| 5,540,647 | A | * | 7/1996 | Weiermann ............ D06F 89/00 493/938 |
| 6,015,934 | A | * | 1/2000 | Lee ..................... B65H 45/22 604/387 |
| 6,241,232 | B1 | * | 6/2001 | Schmitt ................ B65B 63/04 493/413 |
| 6,309,336 | B1 | * | 10/2001 | Muessig ............... B65H 45/12 493/437 |
| 8,256,757 | B2 | | 9/2012 | Imazu et al. |
| 8,590,880 | B2 | | 11/2013 | Imazu et al. |
| 8,771,159 | B2 | | 7/2014 | Imazu et al. |
| 8,844,919 | B2 | * | 9/2014 | Motoyoshi ............ B65H 39/00 270/32 |
| 8,897,691 | B2 | | 11/2014 | Imazu et al. |
| 8,915,490 | B2 | * | 12/2014 | Izumichi .............. B65H 39/00 270/32 |
| 9,085,437 | B2 | | 7/2015 | Shirakura et al. |
| 2016/0193088 | A1 | | 7/2016 | Shimada |

FOREIGN PATENT DOCUMENTS

| | | |
|---|---|---|
| CN | 102190203 A | 9/2011 |
| CN | 102367115 A | 3/2012 |
| CN | 102756943 A | 10/2012 |
| CN | 103662961 A | 3/2014 |
| CN | 203568565 U | 4/2014 |
| DE | 10 2008 001 246 A1 | 10/2009 |
| JP | 2004-248785 A | 9/2004 |
| JP | 2010-235314 A | 10/2010 |
| JP | 2015-067390 A | 4/2015 |
| JP | 2015-096439 A | 5/2015 |
| JP | 6026060 B1 | 11/2016 |

OTHER PUBLICATIONS

Jun. 28, 2020 International Search Report issued in International Patent Application No. PCT/CN2020/084157.

Jan. 27, 2023 extended Search Report issued in European Patent Application No. 20786236.8.

* cited by examiner

FOLDING DEVICE FOR DISPOSABLE HYGIENE ARTICLE

TECHNICAL FIELD

The present invention relates to the field of manufacturing apparatuses for disposable hygiene articles, in particular to the field of manufacturing apparatuses for diapers, feminine hygiene panties, etc., and specifically to a folding device for a disposable hygiene article.

BACKGROUND ART

In the existing folding method and device for a disposable hygiene article, a conveying portion formed by a pair of conveying surfaces that move in the same direction conveys the disposable hygiene article, and the disposable hygiene article is folded by pressing a folding component into the middle part of the disposable hygiene article being conveyed.

The patent document with Chinese Patent Publication No. CN203568565U, entitled "FOLDING DEVICE OF SHEETING STRUCTURE", discloses that a folding component is a plate component, which has a disc portion arranged coaxially with the rotation axis of a rotary shaft and a pair of blades protruding radially outward from the disc portion, wherein the two blades are arranged at an interval of 180° around the rotation axis of the rotary shaft, and the folding component is driven by a driving mechanism to rotate in a mode of sequentially passing through a retracted position and a folding position. The retracted position is a position where contact with a sheeting article led out from lead-out ports of two groups of conveyor belt assemblies (first conveying portion) is avoided. The folding position is a position where the sheeting article is folded by pressing a part (blade) of the folding component into a lead-in port from a position (upper position) at a side opposite the two groups of conveyor belt assemblies (second conveying portion) with respect to the sheeting article led out from the lead-out port and the folded sheeting article is guided to the lead-in port.

The folding component is a blade. The blade rotates around a rotation axis perpendicular to the direction of the second conveying portion, and abuts against the middle part of the sheeting article during folding. Since the sheeting article is pressed into the conveying portion, with the rotation of the blade, the sheeting article and the blade move relative to each other in a direction intersecting with the conveying direction to generate friction, causing the sheeting article to wrinkle and thereby affecting the aesthetic appearance of the folded sheeting article.

SUMMARY

As described above, in the folding device of a sheeting structure disclosed in the above-mentioned patent document, friction is generated between the folding component and the folded sheeting article, causing the sheeting article to wrinkle and thereby affecting the aesthetic appearance of the folded sheeting article. In addition, since the blades are arranged at an interval of 180° around the rotation axis of the rotary shaft, that is, two blades (folding components) alternately fold the sheeting article, the folding speed is limited and high speed folding cannot be achieved.

Therefore, the present invention provides a folding device for disposable hygiene articles capable of avoiding wrinkles when the disposable hygiene articles are folded, thereby affecting the aesthetic appearance of the folded sheeting article.

Moreover, the present invention provides a folding device for a disposable hygiene article, which can achieve high speed folding.

The present invention further provides a folding device for a disposable hygiene article, the device capable of matching disposable hygiene articles of different sizes by simply adjusting the folding device.

In addition, the present invention further provides a folding device for a disposable hygiene article, the device capable of avoiding shakes of the folding device during the process of high speed folding.

The present invention provides a folding device for a disposable hygiene article, comprising: a first conveying portion for conveying the disposable hygiene article along a first path in a state where the disposable hygiene article is sandwiched from front and back sides, and having a lead-out port arranged at a terminal end of the first path; a second conveying portion for conveying, from the terminal end of the first path, the disposable hygiene article along a second path extending in a direction intersecting with the first path in a state where the disposable hygiene article is sandwiched from front and back sides, and having a lead-in port arranged at an initial end of the second path; a folding mechanism having a folding component, which is configured to fold the disposable hygiene article between the first conveying portion and the second conveying portion; a driving mechanism connected to the folding component, which is configured to drive the folding component so that the folding component performs reciprocating linear motion along the direction of the second path between a folding position and a retracted position, wherein the folding position is a position where the disposable hygiene article led out from the lead-out port is folded by pressing a part of the folding component into the lead-in port along the direction of the second path and the folded disposable hygiene article is guided in the lead-in port, and the retracted position is a position where the folding component is away from the lead-in port after the folding component moves linearly in a direction opposite to the second path; and a guiding mechanism for guiding, in an extension direction of the first path or by using an extension line of the first path as a reference, a front end portion of the disposable hygiene article led out from the lead-out port to an opposite side of the second conveying portion in a state where a base end portion of the disposable hygiene article is sandwiched by the first conveying portion from front and back sides. The driving mechanism comprises a plurality of pulleys, at least one servo motor directly connected to any one of the pulleys, and a synchronous belt wrapped around the outer circumference of the plurality of pulleys in a looping path.

The "front and back sides" refer to one side of the disposable hygiene article facing the outside and an opposite side thereof.

The driving mechanism may be a structure enabling the folding component to perform linear reciprocating motion, and may generally be a combination of a pressing component such as a spring and a motor that moves the folding component in accordance with a pressing force, a combination of a motor and a connecting mechanism and so on. In the present invention, a servo motor used as a driving device, can more easily deal with changes in the timing and moving range in which the folding component performs reciprocating motion when changing the size of the disposable hygiene article, and can achieve a high speed. The achievement of a high speed is described below.

The folding component in the folding mechanism is connected to the driving mechanism. The driving mechanism is preferably a combination of the servo motor directly connected to any one of the pulleys and the synchronous belt wrapped around the pulleys in a looping path. At least one of the pulleys of the synchronous belt is driven by the servo motor, and the driving mechanism in the form of the synchronous belt can perform fast reciprocating linear motion together with the folding component in the same direction as the second conveying portion, so that the entire folding mechanism is not worn and has a simple structure and low costs.

Since the driving mechanism adopts the servo motor directly connected to any one of the pulleys, as long as the servo motor rotates forwards and backwards, the linear reciprocating motion of the folding component in the direction of the second conveying portion can be achieved by means of the synchronous belt wrapped around the outer circumference of the pulleys. Furthermore, by controlling the rotation range of the servo motor, the cooperating position of the folding component facing to the synchronous belt can be changed, the range of the reciprocating linear motion of the folding component can be changed, and the change in the size of the hygiene article can be more easily dealt with.

Preferably, the synchronous belt is a toothed belt, and the pulley is also a toothed pulley correspondingly. Further, a core wire of the synchronous belt is preferably made of carbon fibers to satisfy the lightweight characteristics in a high speed state. And preferably, the driving mechanism further comprises guide rollers respectively provided at two sides in the width direction of one side of the synchronous belt in the looping path, for correcting and guiding the synchronous belt in the linear reciprocating motion of the folding component.

Preferably, the folding mechanism further comprises a plurality of rollers arranged on a side of the folding component facing away from a tooth profile of the synchronous belt for cooperating with the linear reciprocating motion of the folding component, the rollers being tangent to the folding component so as to rotate. As a result, when the folding component operates at a high speed, the folding component can operate more stably and smoothly.

Preferably, the folding mechanism further comprises a linkage that connects the synchronous belt to the folding component. The linkage is provided with a sensed portion. The folding mechanism further comprises a first sensor, a second sensor, and a third sensor that are capable of detecting the position of the folding component through the sensed portion, wherein the first sensor is configured to detect a lower limit position of the folding component, the second sensor is configured to detect an upper limit position of the folding component, and the third sensor is configured to detect an origin regression position of the folding component. The position of the sensed portion can be detected by the first sensor, the second sensor, and the third sensor, or the front end portion of the folding component can be directly detected. The sensed portion can also be provided on a reciprocating material, or can be provided at an appropriate position on the folding component or the synchronous belt other than a cooperating component. According to such a structure, the folding component, driven by the servo motor, performs reciprocating linear motion along the direction of the second path by accurate positioning, thereby achieving the reciprocating linear motion along the direction of the second path between the folding position and the retracted position.

Preferably, the folding component is a "Y"-shaped plate structure and comprises a mounting portion attached to the synchronous belt and a folding portion pressed into the lead-in port to fold the disposable hygiene article. The width of the mounting portion is less than the width of the folding portion. This special setting takes into account the balance problem of the folding component in motion, so that no shake is generated in high speed motion.

Preferably, the driving mechanism is controlled by means of a synchronization signal of an encoder or a cam curve.

Preferably, the second path is perpendicular to the first path, and the disposable hygiene article in a flat state is folded by the folding component. In this way, it is prone to generate no wrinkles, thereby facilitating the folding of the disposable hygiene article, and avoiding the problems of asymmetric folding and size deviation of the disposable hygiene article resulting from wrinkles.

The folding device for a disposable hygiene article according to the present invention can prevent the disposable hygiene article from wrinkling during the folding process, thereby effectively ensuring the folding effect. Moreover, the folding device has a simple structure and is easy to be controlled, and can achieve rapid switch of the folding mechanism between a folding position and a retracted position. In addition, the folding device can match disposable hygiene articles of different sizes by adjusting the servo motor, thus providing convenience for product size change. Meanwhile, the folding efficiency is effectively ensured, and the folding device is suitable for high speed folding.

DESCRIPTION OF THE EMBODIMENTS

Figure 2:
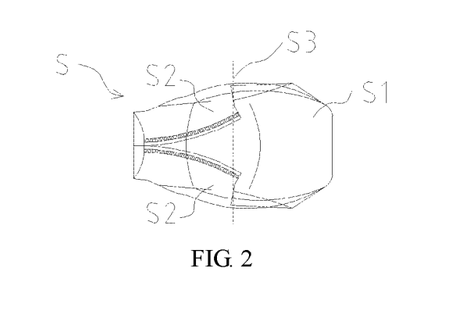
FIG. 2 is a diagram illustrating the structure of a shorts-type diaper serving as a disposable hygiene article in the present invention.
Figure 3:
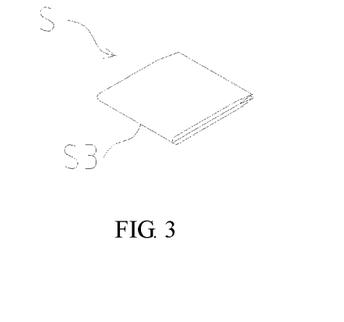
FIG. 3 is a state diagram of the shorts-type diaper shown in FIG. 2 after being folded by the folding device of the present invention.

FIGS. 2 and 3 illustrate an example of a disposable hygiene article folded by a folding device of the present invention, i.e., a shorts-type diaper S. Disposable hygiene articles are necessarily not limited to the shorts-type diaper, but may also be disposable hygiene articles such as waist-attached diapers and feminine hygiene panties.

The shorts-type diaper S includes: an absorbent body S1 for absorbing urine and an elastic waistline S2 connected to the absorbent body S1. The folding device 1 described below is used to fold the shorts-type diaper S along a folding line S3 provided at the central position in the longitudinal direction of the shorts-type diaper S. In this description, the folding line S3 is set at the central position in the longitudinal direction of the shorts-type diaper S as an example, but the folding line S3 can be set at any position on the disposable hygiene article in specific implementation. FIG. 3 illustrates a state of the shorts-type diaper S folded by the folding device 1. It should be noted that during the process of folding the shorts-type diaper S from a state shown in FIG. 2 into a state shown in FIG. 3, the folding of both sides of the elastic waistline S2 of the shorts-type diaper S is achieved in a station process before that of the folding device 1, rather than formed by the folding device 1 of the present invention. The folding device 1 of the present invention folds the shorts-type diaper S along the folding line S3.

Embodiment 1

Figure 1:
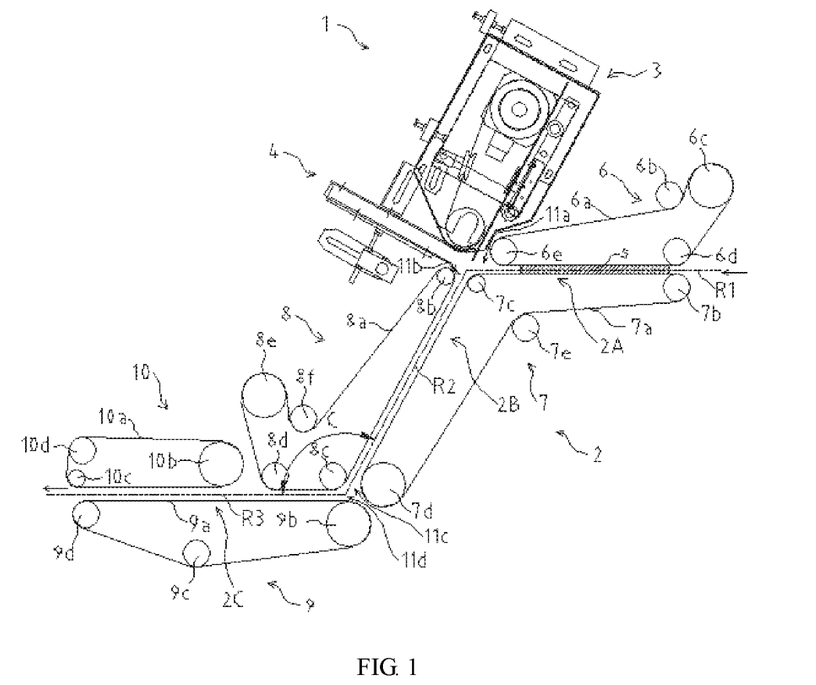
FIG. 1 is a schematic diagram illustrating the overall structure of a folding device of Embodiment 1 of the present invention.

FIG. 1 is a schematic diagram illustrating the overall structure of a folding device of Embodiment 1 of the present invention. Referring to FIG. 1, the folding device 1 of the present invention includes: a conveying mechanism 2 configured to convey the shorts-type diaper S; a folding mechanism 3 configured to fold the shorts-type diaper S conveyed by the conveying mechanism 2; a guide mechanism 4 configured to guide the shorts-type diaper S into a state easy to be folded by the folding mechanism 3; and a support portion 5 for supporting the conveying mechanism 2, the folding mechanism 3, and the guiding mechanism 4.

The conveying mechanism 2 includes: a first belt assembly 6, a second belt assembly 7 for conveying the shorts-type diaper S while sandwiching the shorts-type diaper S with the first belt assembly 6, a third belt assembly 8 for conveying the shorts-type diaper S while sandwiching the shorts-type diaper S with the second belt assembly, a fourth belt assembly 9 for conveying the shorts-type diaper S while sandwiching the shorts-type diaper S with the third belt assembly 8, and a fifth belt assembly 10 for conveying the shorts-type diaper S while sandwiching the shorts-type diaper S with the fourth belt assembly 9.

The first belt assembly 6 includes: a first belt 6a and a plurality of first belt rollers 6b-6e for disposing the first belt 6a in a looping path. The first belt 6a, in a state of being disposed on the first belt rollers 6b-6e, has a portion arranged along a first path R1 parallel to the horizontal direction. The term "parallel" described herein includes a case where the first path R1 is substantially parallel or essentially parallel to the horizontal direction.

The second belt assembly 7 includes: a second belt 7a and a plurality of second belt rollers 7b-7e for disposing the second belt 7a in a looping path. The second belt 7a, in a state of being disposed on the second belt rollers 7b-7e, has a portion arranged along the first path R1 and a portion arranged along a second path R2 inclined with respect to the first path R1. Herein, referring to FIG. 8, the second path R2 is a path extending from a terminal end of the first path R1 in a direction intersecting with the first path R1. An angle formed by the second path R2 and a perpendicular line R12 perpendicular to the first path R1 is an inclination angle A.

Referring to FIG. 1, the third belt assembly 8 includes: a third belt 8a and a plurality of third belt rollers 8b-8f for disposing the third belt 8a in a looping path. The third belt 8a, in a state of being disposed on the third belt rollers 8b-8f, has a portion arranged along the second path R2 and a portion arranged along a third path R3 inclined with respect to the second path R2. Herein, the third path R3 is parallel to the first path R1. The term "parallel" described herein also includes a case where both paths are substantially parallel or essentially parallel. That is, the third path R3 is inclined by an angle C (=angle A+90°) with respect to the second path R2.

The fourth belt assembly 9 includes: a fourth belt 9a and a plurality of fourth belt rollers 9b-9d for disposing the fourth belt 9a in a looping path. The fourth belt 9a, in a state of being disposed on the fourth belt rollers 9b-9d, has a portion arranged along a third path R3.

The fifth belt assembly 10 includes: a fifth belt 10a and a plurality of fifth belt rollers 10b-10d for disposing the fifth belt 10a in a looping path. The fifth belt 10a, in a state of being disposed on the fifth belt rollers 10b-10d, has a portion arranged along the third path R3.

The first belt assembly 6 and the second belt assembly 7 constitute a first conveying portion 2A, and the first conveying portion 2A conveys the shorts-type diaper S along the first path R1 in a state where the shorts-type diaper S is sandwiched from front and back sides. Herein, between the first belt assembly 6 and the second belt assembly 7, a lead-out port 11a is formed at a position regarded as the terminal end of the first path R1.

The second belt assembly 7 and the third belt assembly 8 constitute a second conveying portion 2B, and the second conveying portion 2B conveys the shorts-type diaper S from a lead-in port 11b along the second path R2 in a state where the shorts-type diaper S is sandwiched from front and back sides. Herein, between the second belt assembly 7 and the third belt assembly 8, the lead-in port 11b is formed at a position regarded as an initial end of the second path R2, and a lead-out port 11c is formed at a position regarded as a terminal end of the second path R2.

The third belt assembly 8, the fourth belt assembly 9, and the fifth belt assembly 10 constitute a third conveying portion 2C. The third conveying portion 2C conveys the shorts-type diaper S received from the second conveying portion 2B along the third path R3. Herein, the third path R3 is arranged such that an extension line thereof intersects with the second path R2. Therefore, the third conveying portion 2C can convey the shorts-type diaper S led out from the lead-out port 11c of the second conveying portion 2B along the third path R3 from the lead-in port 11b. In this case, the conveying mechanism 2 conveys the shorts-type diaper S along the first path R1, the second path R2, and the third path R3 in sequence.

Figure 4:
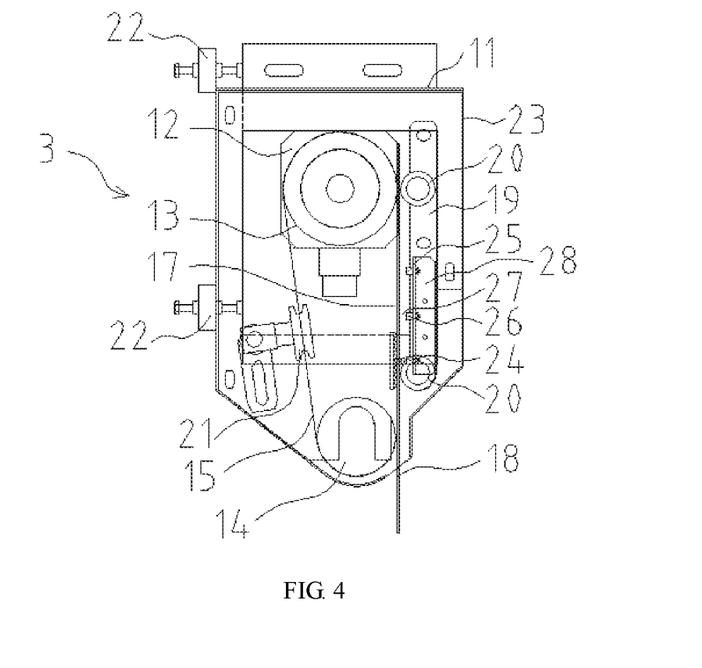
FIG. 4 is a front view of a folding mechanism of Embodiment 1.
Figure 5:
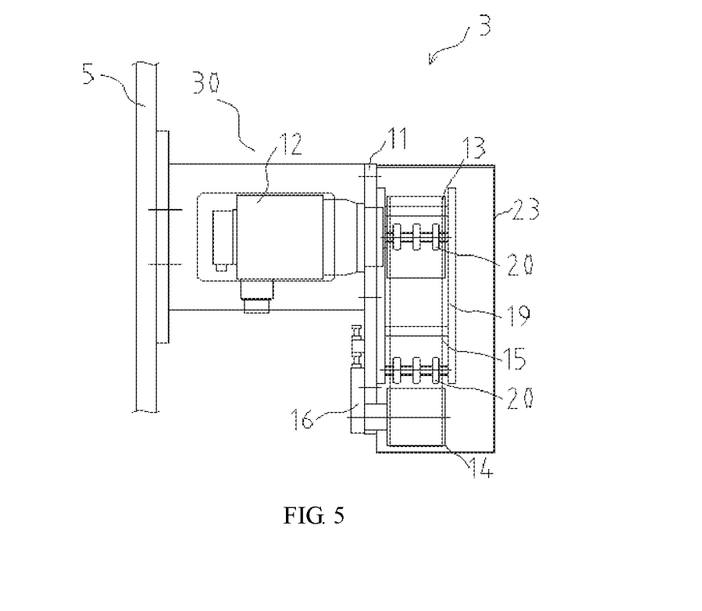
FIG. 5 is a side view of the folding mechanism of Embodiment 1 (mainly showing the roller part).

FIG. 4 and FIG. 5 respectively illustrate a front view and a side view of the folding mechanism of this embodiment. As can be seen from FIG. 4 and FIG. 5, the folding mechanism 3 is used to fold the shorts-type diaper S between the lead-out port 11a of the first conveying portion 2A and the lead-in port 11b of the second conveying portion 2B. Specifically, the folding mechanism 3 includes a folding component 18 for folding the shorts-type diaper S and a driving mechanism 30 that drives the folding component 18 to perform reciprocating linear motion along the direction of the second path R2.

The driving mechanism 30 includes: a servo motor 12 fixed to the support portion 5 by means of a fixing portion 11, a first pulley 13 connected to an output shaft of the servo motor 12 through the fixing portion 11, and a second pulley 14 also fixed at a side of the fixing portion 11 facing away from the servo motor 12. Of course, the second pulley 14 can also be directly driven by another servo motor independent of the servo motor 12. However, in this embodiment, only one servo motor 12 is used as an example for driving. Specifically, the second pulley 14 is mounted at the side of the fixing portion 11 facing away from the servo motor 12 by means of a support portion 16, and it is also possible to adjust the position of the second pulley 14 relative to the fixing portion 11 up and down through the support portion 16 to tension a synchronous belt 15. The first pulley 13 and the second pulley 14 are connected in a looping path by the synchronous belt 15 to move synchronously. The synchronous belt is preferably a toothed belt, and the pulleys also adopt toothed pulleys correspondingly. Preferably, a core wire of the synchronous belt is made of carbon fibers to satisfy the lightweight characteristics in a high speed state. The driving mechanism 30 further includes two guide rollers 21 respectively provided at two sides in the width direction of one side of the synchronous belt 15 in the looping path. The two guide rollers 21 are mounted on the fixing portion 11 by means of a fixing base and are used to correct and guide the synchronous belt 15 during the reciprocating linear motion of the folding component 18.

In the present invention, in order to achieve high speed folding, the driving motor 12 adopted in the driving mechanism 30 is not an ordinary motor, but a motor with a high rotate speed and low inertia, which is suitable for reciprocating motion with a high frequency speed change and forward and reverse rotation.

In addition, the first pulley 13 and the second pulley 14 in the driving mechanism 30 are made of aluminum. The pulley used in the present invention is a relatively small pulley with fewer than 80 teeth. A relatively small pulley has fewer teeth and lighter weight, and is generally made of iron, while a relatively large pulley with greater than 80 teeth is made of aluminum. The size of the pulley is generally classified using the number of teeth, for example, 80 teeth, as demarcation. That is, the relatively small pulley used in the present invention is not made of iron as usual, but made of aluminum. Since the density of aluminum is only ⅓ of that of iron, the present invention greatly reduces the weight of the synchronous pulley, improves the conveying accuracy, realizes lightweight, and therefore is more suitable for high speed operation applications.

Moreover, in the present invention, the synchronous belt 15 arranged in the looping path can be designed with layered materials. For example, the body is made of high strength polyurethane rubber (UR), the core wire is made of carbon fibers, and a tooth portion is made of high strength nylon canvas. The use of carbon fibers in the middle core wire is also to achieve light weight and meet high-speed operation.

As described above, the selection, material and other aspects of the various components in the driving mechanism 30 involved in motion are different from that in the conventional driving mechanism. The setting achieves improved lightweight, especially suitable for high-speed operation applications, so as to realize fast reciprocating linear motion. Meanwhile, the lightweight design can prevent the entire folding mechanism from being worn during high speed operation, and the device is simpler and lower in cost compared with a conventional transmission structure.

Figure 8:
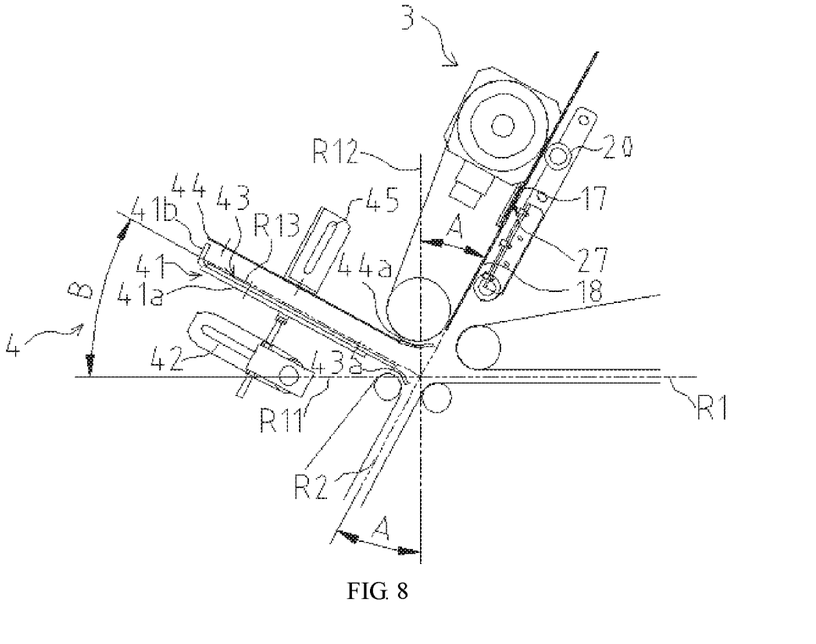
FIG. 8 is a partial view of the folding mechanism part of Embodiment 1.
Figure 10:
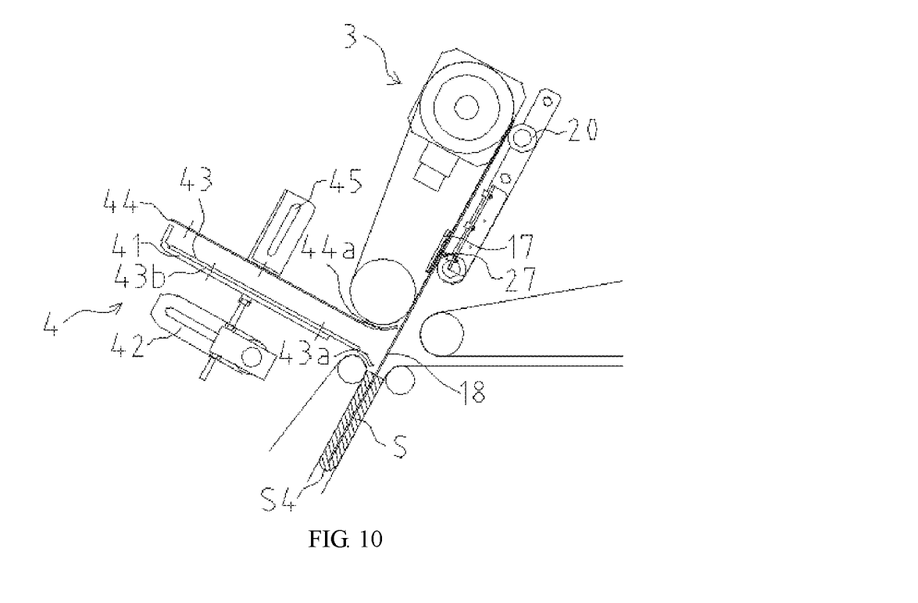
FIG. 10 is a state diagram illustrating that the folding component in the folding device of Embodiment 1 has been driven to the folding position.

The folding component 18 is connected to the driving mechanism 30. Specifically, the folding component 18 is fixed at one side of the synchronous belt 15 (the side opposite the guide roller 21). According to the above structure, in the cases when the servo motor 12 in the driving mechanism 30 rotates forward and reverse, the folding component 18 achieves downward and upward linear motions. When the servo motor 12 rotates clockwise, the first pulley 13 also rotates clockwise, and the folding component 18 moves linearly downward to reach the folding position. The shorts-type diaper S led out from the lead-out port 11a is folded by pressing a part of the folding component 18 into the lead-in port 11b along the direction of the second path R2, and the folded shorts-type diaper S is guided to a position in the lead-in port 11b, achieving a state as shown in FIG. 10. When the servo motor 12 rotates counterclockwise, the first pulley 13 also rotates counterclockwise, and the folding component 18 moves linearly upwards to reach a retracted position, the folding component 18 is away from the position of the lead-in port 11b after the folding component 18 moves linearly in a direction opposite to the direction of the second path R2, achieving a state as shown in FIG. 8.

Figure 6:
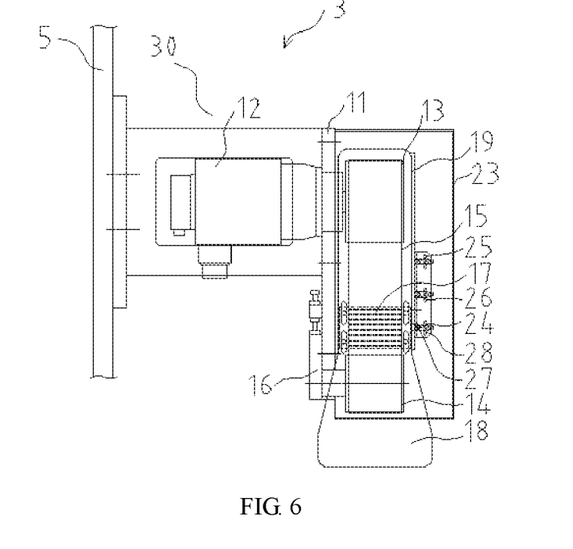
FIG. 6 is a side view of the folding mechanism of Embodiment 1 (mainly showing the folding component and the sensor part).

The folding mechanism 3 also includes a linkage 17 connected to the folding component 18 and arranged at the inner side of the synchronous belt 15. The linkage 17 is connected to the synchronous belt 15, so the linkage 17 is also provided with a tooth profile on a side connected to the synchronous belt 15, the tooth profile matching a tooth profile of the synchronous belt 15, as shown in FIG. 4 and FIG. 6 in detail. The folding component 18 is connected to the synchronous belt 15 by means of the linkage 17. The linkage 17 is further provided with a sensed portion 27, which can be sensed by a sensor described below.

In the present invention, the linkage 17 has a tooth profile corresponding to the tooth profile of the synchronous belt 15 on the side facing to the synchronous belt 15. The linkage 17 is combined with the synchronous belt 15 by means of the tooth profile, and is fixed to the folding component 18 through the synchronous belt 15. That is, the folding component 18 is fixed to the synchronous belt 15 by means of the tooth profile on the linkage 17 and driven by the servo motor 12 to perform reciprocating motion. The ordinary screw connection may loosen during high speed reciprocating motion, while the tooth profile matching transmission mode adopted in the present invention can ensure that the connection between the folding component 18 and the synchronous belt 15 is fully fixed during high speed reciprocating motion, without loosening due to insecure fixation at a high speed, causing no deviation in the position of the folding component 18, ensuring the stability of transmission during the high speed reciprocating motion, and thereby accurately controlling the position of the folding component 18.

In addition, the folding component 18 is completely fixed to the synchronous belt 15 by means of the linkage 17, so that the folding component 18 and the synchronous belt 15 form an integrated body. When the servo motor 12 rotates forward or reverse, the folding component 18 and the synchronous belt 15 serving as an integrated body move upward or downward, without the generation of wear therebetween.

Figure 7:
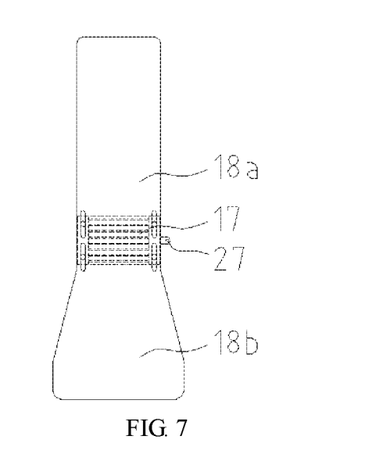
FIG. 7 is a diagram illustrating a mounting relationship and structure of the linkage and the folding component in FIG. 6.

FIG. 7 illustrates a mounting relationship and structure between the linkage 17 and the folding component 18, the synchronous belt 15 between which are not shown. Referring to FIG. 7, the folding component 18 is a "Y"-shaped plate structure, including a mounting portion 18a and a folding portion 18b. The width of the mounting portion 18a attached to the synchronous belt is less than the width of the folding portion 18b for being pressed into the lead-in port 11b to fold the shorts-type diaper S. The width of the folding portion 18b is at least larger than ½ of the width of the shorts-type diaper S, preferably not less than the overall width of the shorts-type diaper S. Of course, in order to satisfy the requirement for lightweight, the width of the folding portion 18b should not be too large. Preferably, the width of the folding portion 18b is greater than the width of the shorts-type diaper S and less than 1.5 times the width of the shorts-type diaper S.

Since the folding component 18 is a "Y"-shaped plate structure, in order to prevent the folding component 18 from shaking due to the high speed during the high frequency reciprocating motion, the width of the folding portion 18b that is in contact with and for folding the shorts-type diaper S is set wider, which can ensure the dynamic balance of the folding component 18. The mounting portion of the folding component 18 adopts a long waist hole structure, so as to facilitate the adjustment of the position of the folding component 18 relative to the synchronous belt 15 in a direction the same as or opposite to the second path R2, and to facilitate the adjustment for folding shorts-type diapers S of different sizes.

Referring to FIG. 5, the folding mechanism 3 further includes a plurality of rollers 20 arranged at a side of the folding component 18 facing away from the tooth profile of the synchronous belt 15 and used to cooperate with the linear reciprocating motion of the folding component 18. Two sets of rollers 20 are arranged vertically, each set including a plurality of rollers. The specific number of the rollers 20 can be determined according to the length and width of the folding component 18, and the two sets of rollers 20 are fixed on the fixing portion 11 through a plate component 19. The rollers 20 can rotate by being tangent to the folding component 18, so that in the case of high speed operation, the folding component 18 operates more stably and smoothly.

Figure 11:
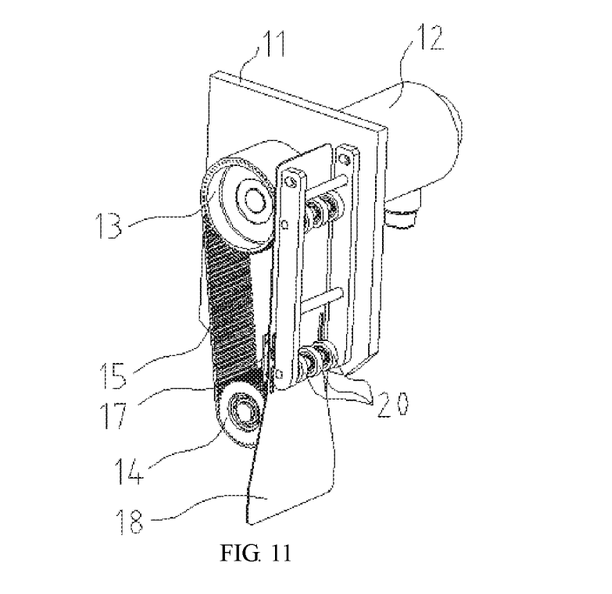
FIG. 11 is a perspective view of the folding mechanism of Embodiment 1.

FIG. 11 is a perspective view of the folding mechanism 3. The positional relationship and connection relationship among the servo motor 12, the first pulley 13, the second pulley 14, the synchronous belt 15, the linkage 17, the folding component 18, and the rollers 20 can be seen directly from the figure.

The folding mechanism 3 also includes a first sensor 24, a second sensor 25, and a third sensor 26 that are mounted on the plate component 19 through a bending member 28. The first sensor 24 is used to detect a lower limit position of the folding component 18. The second sensor 25 is used to detect an upper limit position of the folding component 18. The third sensor 26 is used to detect an origin regression position of the folding component 18. Referring to FIG. 1 and FIG. 10, when the shorts-type diaper S is to be folded, under the clockwise drive of the servo motor 12, the sensed portion 27 on the linkage 17 moves along the direction of the second path R2 with the synchronous belt 15 until it reaches the folding position, in which case the servo motor 12 stops rotating. The first sensor 24 is provided at the lower limit position slightly closer to the downstream side of the second path R2 than the folding position. Normally, when reaching the folding position, the sensed portion 27 stops without being detected by the first sensor 24. If the first sensor 24 detects the sensed portion 27, it indicates that the sensed portion 27 has passed the folding position, and this moment, a detection signal of the first sensor 24 is used as an alarm signal to trigger the servo motor 12 to stop. Referring to FIG. 1 and FIG. 8, after the shorts-type diaper S is folded, the servo motor 12 rotates counterclockwise, and the sensed portion 27 on the linkage 17 moves along the direction opposite to the direction of the second path R2 with the synchronous belt 15 until it reaches the retracted position, in which case the servo motor 12 stops rotating. The second sensor 25 is provided at the upper limit position slightly farther away from the second path R2 than the retracted position. Normally, when reaching the retracted position, the sensed portion 27 stops without being detected by the second sensor 25. If the second sensor 25 detects the sensed portion 27, it indicates that the sensed portion 27 has passed the retracted position, and this moment, a detection signal of the second sensor 25 is used as an alarm signal to trigger the servo motor 12 to stop. Referring to FIG. 1 and FIG. 4, when the device restarts or the folding mechanism 3 needs to be reset, the sensed portion 27 on the linkage 17 moves along the direction of the second path R2 or along the direction opposite to the direction of the second path R2 with the synchronous belt 15 until it is detected by the third sensor 26, in which case the folding component 18 in the folding mechanism 3 returns to an initial setting position. The direction in which the sensed portion 27 moves depends on the position where the folding component 18 is located before resetting.

The driving mechanism 30 drives the folding component 18 to perform reciprocating linear motion between the folding position and the retracted position. A control mode of the driving mechanism 30 may be a mode of a synchronization signal of an encoder or a mode of a cam curve. When the mode of a synchronization signal of an encoder is adopted, values of start synchronization signals of the folding position and the retracted position are separately configured in a control system. Disposable hygiene articles of different sizes correspond to different values of the synchronization signals. When the folding device 1 receives the value of the start synchronization signal of the folding position, and the servo motor 12 is started to rotate clockwise, the folding component 18 linearly moves downward, i.e., towards the folding position. Matching with an operation speed of a production apparatus, when the folding line S3 of the shorts-type diaper S led out from the lead-out port 11a reaches the lead-in port 11b of the second path R2, a part of the folding component 18 is pressed into the lead-in port 11b along the direction of the second path R2, so as to fold the shorts-type diaper S, and the folded shorts-type diaper S is guided to a position in the lead-in port 11b. The degree of pressing a part of the folding component 18 into the lead-in port 11b can be adjusted according to the size of an actual product. When the shorts-type diaper S is folded and the folding device 1 receives the value of the start synchronization signal of the retracted position, the servo motor 12 is started to rotate counterclockwise, and the folding component 18 moves linearly upwards, i.e., towards the retracted position. After the folding component 18 moves linearly along the direction opposite to the direction of the second path, the folding component is away from the position of the lead-in port 11b. In order to fully synchronize the overall paces of the folding mechanism 3 and the folding device 1, the cam curve control mode can be adopted to introduce a designed curve matching the product size into the control system, so that the servo motor 12 operates completely in accordance with a motion trajectory of the curve, in which case the servo motor 12 has a variable speed during the folding process. In actual operation, the control mode can be configured as needed. The cam curve control mode is more accurate and simpler than the conventional control mode of a synchronization signal of an encoder. However, the designing a cam curve is cumbersome, and the curves matching the product sizes may be designed as different ones because of the folding disposable hygiene articles of different sizes, that is, a product size corresponds to a cam curve.

In addition, the folding mechanism 3 further includes: an adjustment portion 22 for adjusting the position of the entire mechanism in a direction perpendicular to the second path R2, and a protective cover 23 mounted at the front end of the mechanism.

Figure 9:
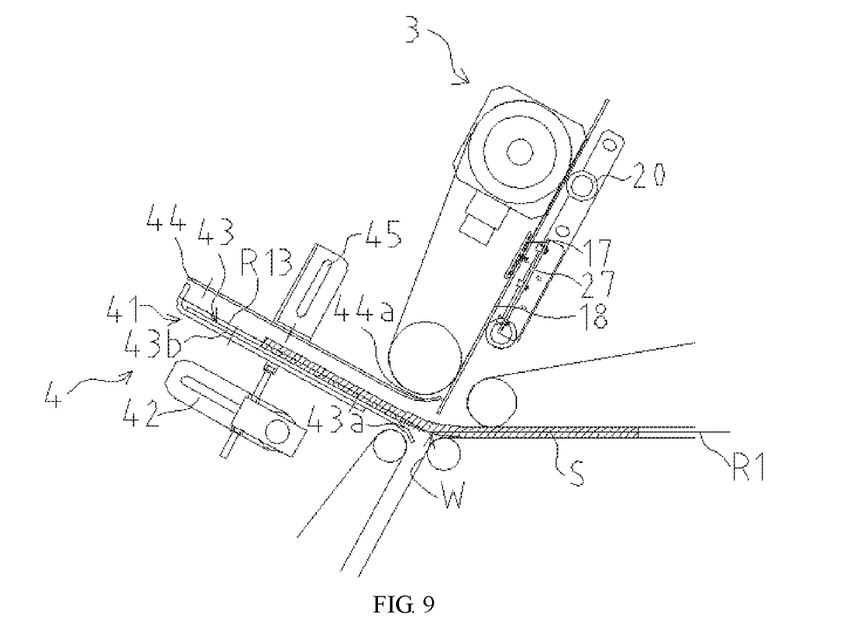
FIG. 9 is a state diagram illustrating that the folding component in the folding device of Embodiment 1 is driven to one of the retracted positions (the folding component at this position is about to enter a folding position).

FIG. 8 and FIG. 9 illustrate partial views of the folding device 1. Referring to FIG. 8 and FIG. 9, the guide mechanism 4 includes: an L-shaped plate 41 fixed to the support portion 5 via a first mounting portion 42, a cover component 44 fixed to the support portion 5 via a second mounting portion 45, and a direction changing component 43 fixed to the L-shaped plate 41. The cover component 44 is located above the direction changing component 43. The L-shaped plate 41 is inclined upward by an angle B with respect to an extension line R11 of the first path R1, and is arranged along an inclined line R13 extending from the terminal end of the first path R1, that is, an angle formed by the extension line R11 and the inclined line R13 is the angle B.

The L-shaped plate 41 includes: an inclined portion 41a fixed to the first mounting portion 42 along the inclined line R13, and a bending portion 41b extending from an upper end portion of the inclined portion 41a in a manner of intersecting with the inclined line R13.

The direction changing component 43 is fixed to the inclined portion 41a, and includes: a first changing surface 43a for changing a movement direction of a front end portion of the shorts-type diaper S by contacting the front end portion of the shorts-type diaper S led out from the lead-out port 11a of the first conveying portion 2A; and a support surface 43b extending from an upper end portion of the first changing surface 43a along the inclined line R13 and supporting the shorts-type diaper S from below, as shown in FIG. 9.

For the shorts-type diaper S in a state where a base end portion thereof is sandwiched from front and back sides by the first conveying portion 2A formed by the first belt assembly 6 and the second belt assembly 7 and led out from the lead-out port 11a, the front end portion of the shorts-type diaper S is guided, using the extension line R11 of the first path R1 as a reference, by the first changing surface 43a in a direction far away from the second conveying portion 2B formed by the second belt assembly 7 and the third belt assembly 8. In order to implement such a function, the distance between the first changing surface 43a and the lead-out port 11a is set to be less than the overall length of the shorts-type diaper S. Furthermore, the first changing surface 43a is a curved surface inclined upward from the extension line R11 (the leftward direction in FIG. 8) of the first path R1, and intersects with the extension line R11.

Therefore, the front end portion of the shorts-type diaper S led out from the lead-out port 11a is in contact with the first changing surface 43a, as shown in FIG. 9, and is guided to the upper side of the extension line R11 of the first path R1, i.e., a side opposite the first belt assembly 6 and the second belt assembly 7. Furthermore, the front end portion of the shorts-type diaper S guided to the upper side of the extension line R11 is supported on the support surface 43b, whereby the front end portion of the shorts-type diaper S is arranged in the direction of the inclined line R13, and accordingly, the shorts-type diaper S located outside the lead-in port 11b forms a bent part W.

Referring to FIG. 8, the cover component 44 covers the direction changing component 43 from above. Specifically, the cover component 44 is a plate component, which is fixed to the support portion 5 by means of the second mounting portion 45. The support portion 5 can move in a direction perpendicular to the inclined line R13, so as to adjust the distance of the cover component 44 from the direction changing component 43. The cover component 44 further includes a second changing surface 44a for changing the movement direction of the front end portion of the shorts-type diaper S by contacting the front end portion of the shorts-type diaper S led out from the lead-out port 11a of the first conveying portion 2A. The second changing surface 44a is bent away from the direction changing component 43, and due to the bending, the front end portion of the shorts-type diaper S can reach between the cover component 44 and the direction changing component 43 strictly along the inclined line R13, thereby facilitating the folding carried out by the folding mechanism 3. The second changing surface 44a is located at the position where the lead-out port 11a is located, and the folding mechanism 3 is located at the position where the lead-out port 11a of the first conveying portion 2A is located and above the second changing surface 44a.

In this embodiment, the sensed portion 27, the first sensor 24, the second sensor 25, and the third sensor 26 are used to detect the position of the folding component 18. However, the present invention is not limited thereto. For example, the position of the folding component 18 can also be detected by means of a rotation angle of a rotary shaft of the servo motor 12.

Embodiment 2

Figure 12:
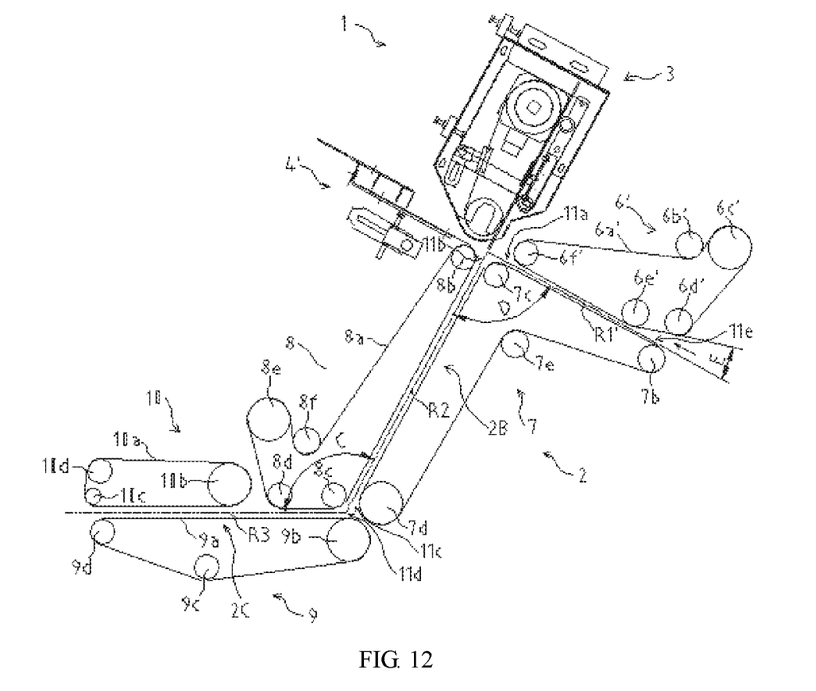
FIG. 12 is a schematic diagram of the overall structure of the folding device of Embodiment 2 of the present invention.

This embodiment differs from Embodiment 1 in a conveying mechanism 2' and a guide limiting mechanism 4'. FIG. 12 is a schematic diagram of the overall structure of a folding device of Embodiment 2. Referring to FIG. 12, similar to that of Embodiment 1, the conveying mechanism 2' of this embodiment also includes: a first belt assembly 6', a second belt assembly 7' for conveying the shorts-type diaper S while sandwiching the shorts-type diaper S with the first belt assembly 6', a third belt assembly 8 for conveying the shorts-type diaper S while sandwiching the shorts-type diaper S with the second belt assembly, a fourth belt assembly 9 for conveying the shorts-type diaper S while sandwiching the shorts-type diaper S with the third belt assembly 8, and a fifth belt assembly 10 for conveying the shorts-type diaper S while sandwiching the shorts-type diaper S with the fourth belt assembly 9.

Figure 13:
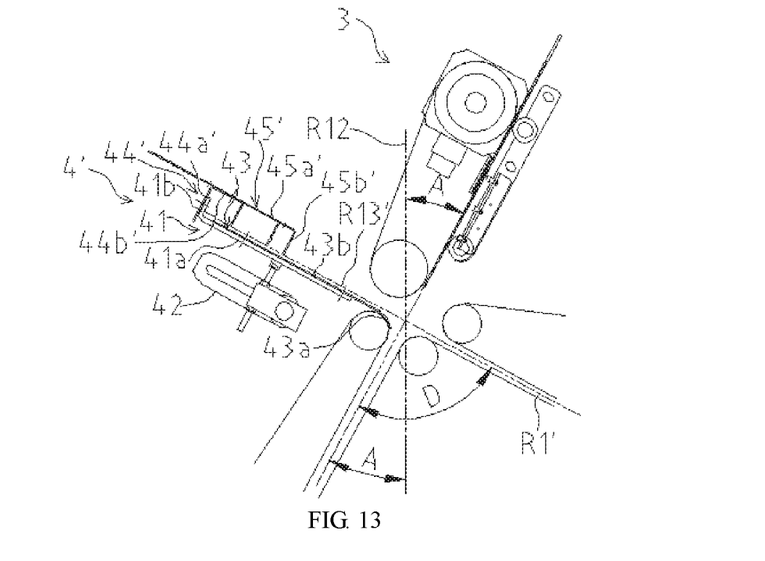
FIG. 13 is a partial view of the folding mechanism part of Embodiment 2.
Figure 14:
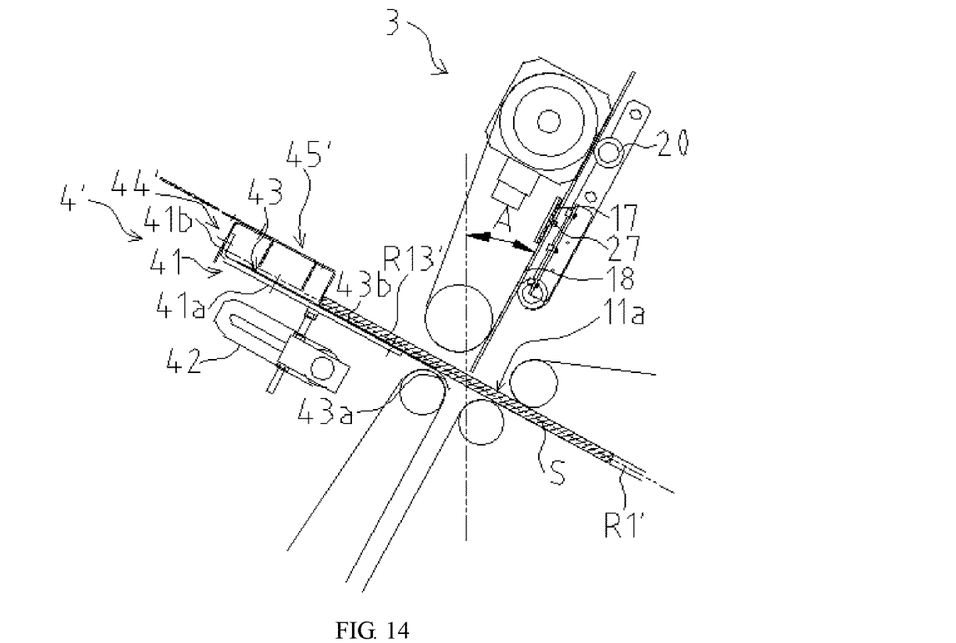
FIG. 14 is a state diagram illustrating that a folding component in the folding device of Embodiment 2 is driven to one of the retracted positions (the folding component at this position is about to enter a folding position).

The first belt assembly 6' different from Embodiment 1 includes: a first belt 6a' and a plurality of first belt rollers 6b'-6f' for disposing the first belt 6a' in a looping path. Referring to FIG. 12, a part of the first belt 6a' between the first belt rollers 6d' and 6e' is arranged to be inclined by an angle E with respect to a first path R1', rather than along the first path R1'. Such an inclined arrangement is equivalent to providing a lead-in opening at the first path R1' of the most upstream side where the shorts-type diaper S enters the folding device 1, so as to ensure that the front end portion of the shorts-type diaper S can enter the folding device 1 more easily. The first belt 6a', in a state of being disposed on the first belt rollers 6b'-6f', has a portion arranged along the first path R1' perpendicular to the folding component 18 of the folding mechanism 3. That is, referring to FIG. 13, an angle formed by the first path R1' and the folding component 18 is D=90°. The term "perpendicular" described herein also includes a case where the first path R1' is substantially perpendicular or essentially perpendicular to the folding component 18. An extension line R13' extending along the first path R1' enables the shorts-type diaper S to be in a straight line state when it travels to the folding position at the lead-in port 11b. Since the first path R1' is perpendicular to the folding component 18, folding the shorts-type diaper S in the straight state from the vertical direction facilitates the folding. Such a state is shown in FIG. 14.

The reasons why folding the shorts-type diaper S in the straight state from the vertical direction can facilitate the folding are explained below. Firstly, before entering the folding device 1 of the present invention, the disposable hygiene articles (shorts-type diapers S in this embodiment) are formed and arranged one by one, that is, the disposable hygiene articles are arranged at intervals. Secondly, since the disposable hygiene article is a sheeting fabric having a certain degree of flexibility and made of a plurality of materials such as non-woven fabrics, different from articles with a certain degree of hardness, such as paper, the disposable hygiene article may be affected by a configured angle of the device in the conveying process. For example, in Embodiment 1, after passing through the first path R1, the front end portion of the disposable hygiene article enters and adheres to the direction changing component 43 of the guide mechanism 4. Since the first path R1 and the direction changing component 43 are not on the same horizontal line but have a certain angle, due to the softness of the disposable hygiene article, when the front end portion thereof enters the direction changing component 43 of the guide mechanism 4, the front end portion does not change its trajectory easily and thus is prone to wrinkling or becoming a non-stretched state. After bent by the folding device, the folded disposable hygiene article may be folded asymmetrically, that is, the two edges of the disposable hygiene article are not aligned, with one edge being longer and the other edge being shorter. If the configuration provided in Embodiment 2 is adopted, since the first path R1' and the direction changing component 43 in the guide limiting mechanism 4' are on the same horizontal line, the product is "lying straight" on the first path R1' and the direction changing component 43, thus avoiding or at least improving the asymmetric folding case described above.

Embodiment 2 further differs from Embodiment 1 in the guide limiting mechanism 4'. Referring to FIG. 13, the guide limiting mechanism 4' includes: an L-shaped plate 41 fixed to the support portion 5 through the first mounting portion 42; the direction changing component 43, a support 44', and a limiting member 45' that are fixed to the L-shaped plate 41. The L-shaped plate 41 is arranged in parallel with an extension line R13' of the first path R1'.

The L-shaped plate 41 includes: an inclined portion 41a fixed to the first mounting portion 42 along the extension line R13' of the first path R1', and a bending portion 41b extending from an upper end portion of the inclined portion 41a in a manner of intersecting with the extension line R13'.

The direction changing component 43 is fixed on the inclined portion 41a. The direction changing component 43 includes: a first changing surface 43a for changing the movement direction of the front end portion of the shorts-type diaper S by contacting the front end portion of the shorts-type diaper S led out from the lead-out port 11a of the first conveying portion 2A; and a support surface 43b extending from an upper end portion of the first changing surface 43a along the extension line R13' and supporting the shorts-type diaper S from below.

The support 44' includes: a mounted portion 44a' connected to the bending portion 41b of the L-shaped plate 41, and a third mounting portion 44b' perpendicular to the mounted portion 44a'. The mounted portion 44a' faces to the position of the lead-in port 11b. That is, the support 44' is also an L-shaped structure and is fixed to the bending portion 41b of the L-shaped plate 41.

The limiting member 45' includes an adjustment mounting portion 45a' and a contact portion 45b'. The limiting member 45' is mounted on the support 44' in an adjustable manner. Specifically, the adjustment mounting portion 45a' is connected to the third mounting portion 44b' of the support 44'. The adjustment mounting portion 45a' and the contact portion 45b' present an L-shaped bending shape, and the contact portion 45b' is bent towards the position of the direction changing component 43. The adjustment mounting portion 45a' can be provided with a long waist hole. The to-be-folded shorts-type diaper S located at the lead-in port 11b is in a straight line state, and the contact portion 45b' is in contact with the front end portion of the shorts-type diaper S, so as to limit the position of the front end portion of the shorts-type diaper S. The position of the waist hole of the adjustment mounting portion 45a' on the limiting member 45' is adjusted to correspond to the front end position of shorts-type diapers S of different sizes. Thus, for example, if the production size of the shorts-type diaper S is changed from size M to size L, the limiting member 45' is adjusted to a position away from the folding mechanism 3, so as to match the shorts-type diaper S of size L.

FIG. 14 is a state diagram of the folding component in the folding device of this embodiment which is driven to one of the retracted positions. As in the state of Embodiment 1 shown in FIG. 9, at this position, the folding component is about to enter the folding position.

Figure 15:
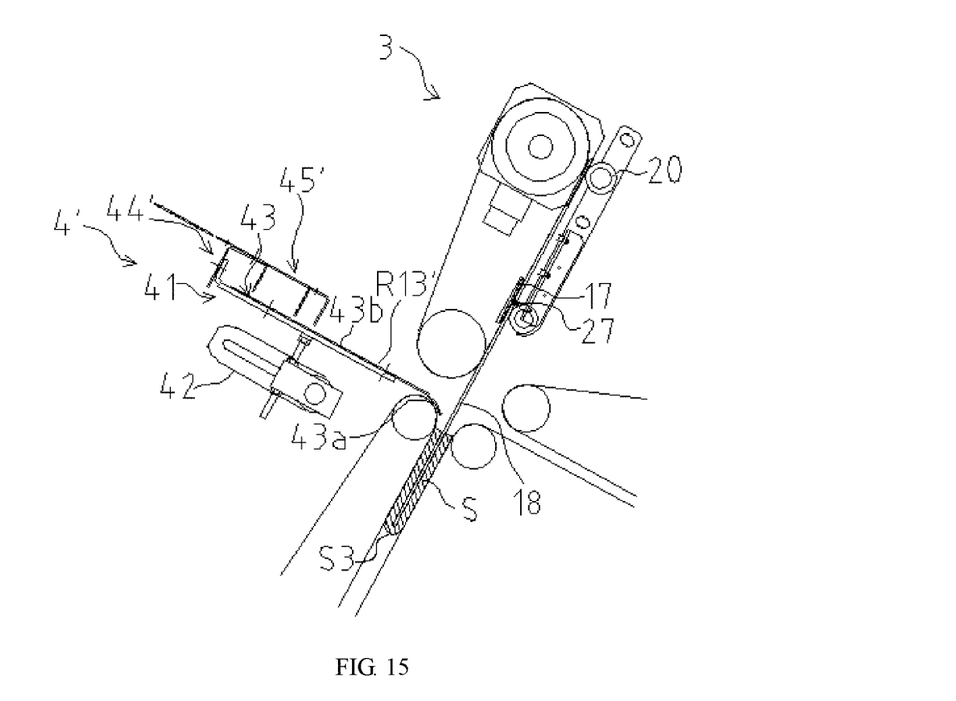
FIG. 15 is a state diagram illustrating that the folding component in the folding device of Embodiment 2 has been driven to the folding position.

FIG. 15 is a state diagram of the folding component 18 in the folding device 1 of this embodiment which has been driven to the folding position. Referring to FIG. 15, the shorts-type diaper S led out from the lead-out port 11b is folded by pressing a part of the folding component 18 into the lead-in port 11b along the direction of the second path R2, and the folded shorts-type diaper S is guided to a position in the lead-in port 11b, so as to reach the folding position.

INDUSTRIAL APPLICABILITY

The folding device for a disposable hygiene article provided by the present invention can prevent a disposable hygiene article from wrinkling during the folding process, thereby effectively ensuring the folding effect. In addition, the folding device can match disposable hygiene articles of different sizes by adjusting the servo motor, thus providing convenience for production of products of different sizes while effectively ensuring the folding efficiency. The folding device is suitable for high speed folding applications, applicable to production lines of disposable hygiene articles such as shorts-type or waist-attached diapers and feminine hygiene panties, and thus has industrial applicability.

What is claimed is:

1. A folding device for a disposable hygiene article, comprising:
   a first conveying portion for conveying the disposable hygiene article along a first path in a state where the disposable hygiene article is sandwiched from front and back sides, and having a lead-out port arranged at a terminal end of the first path;
   a second conveying portion for conveying, from the terminal end of the first path, the disposable hygiene article along a second path extending in a direction intersecting with the first path in a state where the disposable hygiene article is sandwiched from front and back sides, and having a lead-in port arranged at an initial end of the second path;
   a folding mechanism having a folding component, which is configured to fold the disposable hygiene article between the first conveying portion and the second conveying portion;
   a driving mechanism connected to the folding component, which is configured to drive the folding component so that the folding component performs reciprocating linear motion along the direction of the second path between a folding position and a retracted position, wherein the folding position is a position where the disposable hygiene article led out from the lead-out port is folded by pressing a part of the folding component into the lead-in port along the direction of the second path and the folded disposable hygiene article is guided in the lead-in port, and the retracted position is a position where the folding component is away from the lead-in port after the folding component performs linear motion in a direction opposite to the second path; and
   a guiding mechanism that includes an L-shaped plate and a direction changing component fixed to the L-shaped plate for changing a movement direction of a front end portion of the disposable hygiene article, the guiding mechanism configured for guiding, in an extension direction of the first path or by using an extension line of the first path as a reference, a front end portion of the disposable hygiene article led out from the lead-out port to an opposite side of the second conveying portion in a state where a base end portion of the disposable hygiene article is sandwiched by the first conveying portion from front and back sides,
   wherein the driving mechanism comprises a plurality of pulleys, at least one servo motor directly connected to any one of the pulleys, and a synchronous belt wrapped around the outer circumference of the plurality of pulleys in a looping path.

2. The folding device for a disposable hygiene article according to claim 1, wherein the synchronous belt is a toothed belt, and the pulley is a toothed pulley.

3. The folding device for a disposable hygiene article according to claim 1, wherein a core wire of the synchronous belt is made of carbon fibers.

4. The folding device for a disposable hygiene article according to claim 1, wherein the driving mechanism further comprises guide rollers respectively arranged on both sides of the width direction of the synchronous belt in the looping path on a side opposite to the folding component, and configured to correct and guide the synchronous belt during the linear reciprocating motion of the folding component.

5. The folding device for a disposable hygiene article according to claim 2, wherein the folding mechanism further comprises a plurality of rollers located outside the looping path and arranged on a side opposite to the synchronous belt and the pulley with the folding component as a reference, and configured belt for cooperating with the linear reciprocating motion of the folding component, the rollers being tangent to the folding component so as to rotate.

6. The folding device for a disposable hygiene article according to claim 1, wherein the folding mechanism further comprises a linkage that connects the synchronous belt to the folding component.

7. The folding device for a disposable hygiene article according to claim 6, wherein
   the linkage is further provided with a sensed portion,
   the folding mechanism further comprises a first sensor, a second sensor, and a third sensor that are capable of detecting the position of the folding component through the sensed portion, wherein the first sensor is configured to detect a lower limit position of the folding component, the second sensor is configured to detect an upper limit position of the folding component, and the third sensor is configured to detect an origin regression position of the folding component.

8. The folding device for a disposable hygiene article according to claim 1, wherein the folding component is a "Y"-shaped plate structure and comprises a mounting portion attached to the synchronous belt and a folding portion pressed into the lead-in port to fold the disposable hygiene article, and the width of the mounting portion is less than the width of the folding portion.

9. The folding device for a disposable hygiene article according to claim 1, wherein the driving mechanism is controlled by means of a synchronization signal of an encoder or a cam curve.

10. The folding device for a disposable hygiene article according to claim 1, wherein the second path is perpendicular to the first path, and the disposable hygiene article in a flat state is folded by the folding component.

* * * * *